United States Patent
Mertens

(10) Patent No.: US 7,622,417 B2
(45) Date of Patent: Nov. 24, 2009

(54) SYNTHESIS AND USE OF AEI STRUCTURE-TYPE MOLECULAR SIEVES

(75) Inventor: Machteld Maria Mertens, Boortmeerbeek (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/053,044

(22) Filed: Mar. 21, 2008

(65) Prior Publication Data

US 2009/0238745 A1    Sep. 24, 2009

(51) Int. Cl.
*B01J 27/182*    (2006.01)
*C07C 2/00*    (2006.01)
*C07C 5/00*    (2006.01)

(52) U.S. Cl. .................. 502/214; 502/208; 502/500; 423/22; 423/111; 423/327.1; 423/328.1

(58) Field of Classification Search .............. 423/22, 423/111, 114, 327.1, 328.1; 502/214, 208, 502/500

See application file for complete search history.

(56) References Cited

U.S. PATENT DOCUMENTS

| | | | |
|---|---|---|---|
| 4,713,227 A | 12/1987 | Derouane et al. | |
| 5,095,163 A | 3/1992 | Barger | |
| 5,368,836 A * | 11/1994 | Grebner et al. ............. | 423/706 |
| 6,334,994 B1 | 1/2002 | Wendelbo et al. | |
| 7,008,610 B2 | 3/2006 | Cao et al. | |
| 7,090,814 B2 | 8/2006 | Mertens et al. | |
| 7,459,136 B2 | 12/2008 | Mertens | |
| 2002/0165090 A1 * | 11/2002 | Janssen et al. ............. | 502/214 |
| 2003/0153799 A1 * | 8/2003 | Mertens et al. ............. | 585/639 |
| 2005/0096214 A1 | 5/2005 | Janssen et al. | |
| 2005/0233895 A1 | 10/2005 | Mertens et al. | |
| 2006/0292053 A1 | 12/2006 | Mertens et al. | |
| 2007/0203385 A1 | 8/2007 | Chang et al. | |

FOREIGN PATENT DOCUMENTS

| | | |
|---|---|---|
| EP | 1 365 992 | 12/2003 |
| WO | WO 02/070407 | 12/2002 |
| WO | WO 2005/103204 | 11/2005 |
| WO | WO 2007/142745 | 12/2007 |

OTHER PUBLICATIONS

Wilson, Stephen T., Verified Syntheses of Zeolitic Materials. Templating in Molecular Sieve Synthesis [online] 2nd revised edition. UOP Research Center. [retrieved on Aug. 7, 2009]. Retrieved from the Internet: <URL: http://www.iza-online.org/synthesis/VS$_{13}$ 2ndEd/Templating.htm>.

* cited by examiner

*Primary Examiner*—Jerry Lorengo
*Assistant Examiner*—Carlos Barcena
(74) *Attorney, Agent, or Firm*—Kevin M. Faulkner; David M. Weisberg

(57) ABSTRACT

A method is disclosed of synthesizing an aluminophosphate or metalloaluminophosphate molecular sieve comprising an AEI structure type material, in which the rate of heating to the crystallization temperature is controlled, either alone or in combination with the $H_2O:Al_2O_3$ molar ratio of the synthesis mixture, so as to enhance the yield of the desired molecular sieve product.

7 Claims, No Drawings

SYNTHESIS AND USE OF AEI STRUCTURE-TYPE MOLECULAR SIEVES

FIELD OF THE INVENTION

This invention relates to the synthesis of crystalline aluminophosphate and metalloaluminophosphate molecular sieves comprising AEI structure type materials and their use in the conversion of oxygenates, particularly methanol, to olefins, particularly ethylene and propylene.

BACKGROUND OF THE INVENTION

The conversion of oxygenates to olefins (OTO) is currently the subject of intense research, because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as silicoaluminophosphates of the CHA structure, such as SAPO-34. These molecular sieves have cages that are sufficiently large to accommodate aromatic intermediates, while still allowing the diffusional transport of reactants and products into and out of the crystals through regularly interconnected window apertures. By complementing such morphological characteristics with appropriate levels of acid strength and acid density, working catalysts are produced. Extensive research in this area indicates that silicoaluminophosphates are currently more effective OTO catalysts than aluminosilicates. In particular, the control of the silica to alumina molar ratio is a key requirement for the use of aluminosilicates in OTO reactions.

Molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the Atlas of Zeolite Framework Types, 5th edition, Elsevier, London, England (2001).

One known molecular sieve for which a structure has been established is the material designated as AEI, which is a molecular sieve having pores defined by two sets of generally perpendicular channels each having a cross-sectional dimension about 3.8 Å. Molecular sieves of the AEI framework type do not exist in nature, but a number of aluminophosphates and metalloaluminophosphates having the AEI framework type have been synthesized, including SAPO-18, ALPO-18, and RUW-18. Moreover, because of their small pore size, AEI-type molecular sieves have been reported as suitable catalysts for a variety of important chemical processes, including the conversion of oxygenates to olefins. See, for example, U.S. Pat. No. 5,095,163, incorporated herein by reference.

Regular crystalline molecular sieves, such as the AEI and CHA structure type materials discussed above, are built from structurally invariant building units, called Periodic Building Units, and are periodically ordered in three dimensions. However, in addition to pure phase molecular sieves, disordered structures showing periodic ordering in less than three dimensions are also known. One such disordered structure is a disordered planar intergrowth in which the building units from more than one structure type are present. Of particular interest are the intergrowths of containing both AEI and CHA structure type materials since these molecular sieves promise to be particularly attractive catalysts for OTO reactions.

International Patent Publication No. WO 02/70407, published Sep. 12, 2002, and incorporated herein by reference, discloses a silicoaluminophosphate molecular sieve, now designated EMM-2, comprising at least one intergrown phase of molecular sieves having AEI and CHA framework types, wherein said intergrown phase has an AEI/CHA ratio of from about 5/95 to 40/60 as determined by DIFFaX analysis, using the powder X-ray diffraction pattern of a calcined sample of said silicoaluminophosphate molecular sieve. Synthesis of the intergrown material is achieved by mixing reactive sources of silicon, phosphorus, and a hydrated aluminum oxide in the presence of an organic directing agent, particularly a tetraethylammonium compound. The resultant mixture is stirred and heated at a rate of 22-35° C./hour to a crystallization temperature, preferably from 150° C. to 185° C., and then maintained at this temperature under stirring for between 2 and 150 hours. The resultant EMM-2 material is shown to be an active and selective catalyst for converting methanol to light olefins.

U.S. Pat. No. 6,334,994, also incorporated herein by reference, discloses a silicoaluminophosphate molecular sieve, referred to as RUW-19, which is also said to be an AEI/CHA mixed phase composition. In particular, RUW-19 is reported as having peaks characteristic of both AEI and CHA structure type molecular sieves, except that the broad feature centered at about 16.9 (2θ) in RUW-19 replaces the pair of reflections centered at about 17.0 (2θ) in AEI materials and RUW-19 does not have the reflections associated with CHA materials centered at 2θ values of 17.8 and 24.8. DIFFaX analysis of the X-ray diffraction pattern of RUW-19, as produced in Examples 1, 2, and 3 of U.S. Pat. No. 6,334,994, indicates that these materials are characterized by single intergrown phases of AEI and CHA structure type molecular sieves with AEI/CHA ratios of about 60/40, 65/35 and 70/30. Again RUW-19 is reported to be active as a catalyst in the production of light olefins from methanol.

U.S. Patent Application Publication No. 2005/0233895, published Oct. 20, 2005, discloses a silicoaluminophosphate molecular sieve that comprises first and second intergrown phases of a CHA framework type and an AEI framework type, wherein said first intergrown phase has an AEI/CHA ratio of from about 5/95 to about 40/60 as determined by DIFFaX analysis, the second intergrown phase has an AEI/CHA ratio of about 30/70 to about 55/45 as determined by DIFFaX analysis and the molecular sieve has a silica to alumina molar ratio ($Si/Al_2$) from about 0.13 to about 0.24. In Example 1, the molecular sieve was produced by heating a mixture of phosphoric acid, demineralized water, tetraethylammonium hydroxide solution, Ludox AS 40 (40% silica), and alumina having the following composition:

in a stainless steel autoclave at a rate of 20° C./hour to 165° C. and then holding at this temperature for 60 hours.

One of problems involved in the synthesis of aluminophosphate and metalloaluminophosphate molecular sieves, such as those comprising AEI structure type materials and, in particular, those comprising intergrowths of both AEI and CHA structure type materials, is the low product yield typically obtained in the synthesis process. For example, existing synthesis routes often achieve yields as low as 15 wt %, based on the solids added to the reaction mixture. Moreover, although a variety of methods have been proposed to increase yield, such as increasing crystallization temperature, as well as prolonging time at the crystallization temperature, these methods are often accompanied by an undesirable increase in the production of impurity phases. There is, therefore, significant interest in finding alternative methods of increasing product yield. According to the present invention, it has now been found that product yield in the synthesis of aluminophosphate and metalloaluminophosphate molecular sieves comprising AEI structure type materials can be increased by decreasing the rate of heating to the desired crystallization temperature, especially when the water content of the reaction mixture is also reduced.

U.S. Patent Application Publication No. 2007/0203385, published Aug. 30, 2007, discloses that the attrition resistance index of a metalloaluminophosphate molecular sieve can be adjusted by control of its morphology and size index (MSI). In particular, the Examples show that, when crystallizing an AEI/CHI intergrown silicoaluminophosphate molecular sieve from a mixture of water, 85% phosphoric acid, colloidal silica, pseudoboehmite, and tetraethylammonium hydroxide (TEAOH) having the composition:

reducing the heating rate to the crystallization temperature from 13° C./hour to 6.4° C./hour can reduce the MSI of the product. No information is provided as to the effect of the heating rate on the yield of the molecular sieve.

U.S. Pat. No. 7,008,610 discloses synthesis of a crystalline aluminosilicate material having an AEI framework type in the presence of a halogen compound, such as a fluoride, and N,N-diethyl-2,6-dimethylpiperidinium cations as the structure directing agent. In Example 1, a yield of AEI framework type molecular sieve of 28.3 wt %, based on the weight of the dry gel was obtained, although it will be seen that the molecular sieve produced by this patent is substantially free of framework phosphorus.

SUMMARY OF THE INVENTION

In one aspect, the invention resides in a method of synthesizing an aluminophosphate or metalloaluminophosphate molecular sieve comprising an AEI structure type material, the method comprising: (a) preparing a mixture comprising a source of water, a source of aluminum, optionally a source of a metal other than aluminum, a source of phosphorus, and at least one organic directing agent for directing the formation of said molecular sieve; (b) heating said mixture to a crystallization temperature of between about 150° C. and about 200° C., wherein at least part of said heating is conducted so as to raise the temperature of said mixture at a rate of less than or equal to 6.0° C. per hour, such as at a rate of between about 2° C. per hour and about 5° C. per hour; (c) maintaining said mixture at said crystallization temperature for a period of time from about 2 to about 150 hours; and (d) recovering said molecular sieve.

Conveniently, said mixture in (a) has a $H_2O:Al_2O_3$ molar ratio less than 40, such as between about 10 to about 25.

In a further aspect, the invention resides in a method of synthesizing an aluminophosphate or metalloaluminophosphate molecular sieve comprising an AEI structure type material, the method comprising: (a) preparing a mixture comprising a source of water, a source of aluminum, optionally a source of a metal other than aluminum, a source of phosphorus, and at least one organic directing agent (R) for directing the formation of said molecular sieve, said mixture having the following molar composition:

$P_2O_5: Al_2O_3$ from about 0.6 to about 1.2,
R: $Al_2O_3$ from about 0.5 to about 2, and
$H_2O:Al_2O_3$ less than 30;

(b) heating said mixture to a crystallization temperature of between about 150° C. and about 200° C., wherein at least part of said heating is conducted so as to raise the temperature of said mixture at a rate of less than or equal to 20° C. per hour, such as at a rate of between about 2° C. per hour and about 15° C. per hour, for example at a rate of between about 2° C. per hour and about 5° C. per hour; (c) maintaining said mixture at said crystallization temperature for a period of time from about 2 to about 150 hours; and (d) recovering said molecular sieve.

Conveniently, said mixture in (a) has a $H_2O:Al_2O_3$ molar ratio between about 10 to about 25.

Conveniently, said mixture includes a source of an oxide of a metal, M, other than aluminum having a valence n and the mixture (a) has a $M_{n/2}O: Al_2O_3$ ratio of from about 0.005 to about 0.6. Generally, the metal M is silicon.

Conveniently, said at least one organic directing agent comprises a tetraethylammonium compound and optionally further comprises dipropylamine.

Conveniently, said crystallization temperature is between about 150° C. and 175° C., for example between about 155° C. and about 170° C.

Conveniently, said crystallization time in (c) is from about 5 hours to about 100 hours, such as from about 10 hours to about 50 hours.

Conveniently, said mixture is agitated during (b) and (c).

Conveniently, said recovering (d) comprises separating said molecular sieve from said mixture to leave a mother liquor, and recycling at least part of the mother liquor to said mixture (a).

In yet a further aspect, the invention resides in a method of synthesizing an aluminophosphate or metalloaluminophosphate molecular sieve comprising at least one intergrown phase of an AEI structure type material and a CHA structure type material, the method comprising crystallizing a reaction mixture comprising a source of water, a source of aluminum, optionally a source of a metal other than aluminum, a source of phosphorus, and at least one organic directing agent (R) for directing the formation of said molecular sieve, wherein the conditions of said crystallizing are controlled so that the yield of said molecular sieve is at least 18 wt %, such as at least 20 wt %, of the solids content of the reaction mixture.

In still yet a further aspect, the invention resides in an aluminophosphate or metalloaluminophosphate molecular sieve comprising an AEI structure type material, such as at least one intergrown phase of an AEI structure type material and a CHA structure type material, produced by the method described herein.

In another aspect, the invention resides in a process for making an olefin product from an oxygenate feedstock comprising contacting said oxygenate feedstock with a catalyst comprising an aluminophosphate or metalloaluminophosphate molecular sieve produced by the method described herein.

In another aspect, the invention also resides in a method of synthesizing an aluminophosphate or metalloaluminophosphate molecular sieve comprising an AEI structure type material, the method comprising: (a) preparing a mixture comprising a source of water, a source of aluminum, a source of phosphorus, and at least one directing agent; (b) heating said mixture to a crystallization temperature within a range of from about 150° C. to about 200° C., wherein at least part of said heating is conducted so as to raise the temperature of said mixture at a rate of 6.0° C. per hour or less, in one embodiment a non-zero rate, said temperature raising extending for at least one hour; (c) maintaining said mixture within the crystallization temperature range for a time of at least 2 hours; and (d) recovering said molecular sieve.

In another aspect, the invention also resides in a method of synthesizing an aluminophosphate or metalloaluminophosphate molecular sieve comprising an AEI structure type material, the method comprising: (a) preparing a mixture comprising a source of water, a source of aluminum, a source of phosphorus, and at least one directing agent; (b) heating said mixture to a crystallization temperature of at least about 150° C., wherein at least part of said heating is conducted so as to raise the temperature of said mixture at a rate of 6.0° C. per hour or less, in one embodiment a non-zero rate, said temperature raising extending for at least one hour; (c) maintaining said mixture at the crystallization temperature for a time of at least 2 hours; and (d) recovering said molecular sieve.

DETAILED DESCRIPTION OF THE PREFERRED EMBODIMENTS

The present invention relates to a method of synthesizing an aluminophosphate or metalloaluminophosphate molecular sieve comprising an AEI structure type material. Also disclosed herein is the use of the resultant molecular sieve in a process for the conversion of oxygenates, particularly methanol, to olefins, particularly ethylene and propylene.

The aluminophosphate or metalloaluminophosphate molecular sieve produced by the present method may be a single phase AEI structure type material, or may be a composition comprising an AEI structure type molecular sieve together with other structure type materials present as, for example, impurity phases, or may a molecular sieve comprising an intergrowth of an AEI structure type material with a different structure type material, such as a CHA structure type.

Examples of single phase AEI structure type molecular sieves include SAPO-18, ALPO-18 and RUW-18. The preparation and characterization of these molecular sieves and other AEI structure type materials have been reported in several publications, including U.S. Pat. No. 4,440,871; J. Chen et al in "Studies in Surface Science and Catalysis", Vol. 84, pp. 1731-1738; U.S. Pat. No. 5,279,810; J. Chen et al. in "Journal of Physical Chemistry", Vol. 98, pp. 10216-10224 (1994); J. Chen et al in "Catalysis Letters", Vol. 28, pp. 241-248 (1994); pp. 2291-2296 (1994); Yan Xu et al. in "Journal of the Chemical Society, Faraday Transactions" Vol. 86(2), pp. 425-429 (1990); and U.S. Pat. No. 5,609,843. The entire contents of these publications are incorporated herein by reference.

Intergrown molecular sieve phases are disordered planar intergrowths of molecular sieve frameworks. Reference is directed to the "Catalog of Disordered Zeolite Structures", 2000 Edition, published by the Structure Commission of the International Zeolite Association and to the "Collection of Simulated XRD Powder Patterns for Zeolites", M. M. J. Treacy and J. B. Higgins, 2001 Edition, published on behalf of the Structure Commission of the International Zeolite Association for a detailed explanation on intergrown molecular sieve phases.

Regular crystalline solids are built from structurally invariant building units, called Periodic Building Units, and are periodically ordered in three dimensions. Structurally disordered structures show periodic ordering in dimensions less than three, i.e., in two, one, or zero dimensions. This phenomenon is called stacking disorder of structurally invariant Periodic Building Units. Crystal structures built from Periodic Building Units are called end-member structures if periodic ordering is achieved in all three dimensions. Disordered structures are those where the stacking sequence of the Periodic Building Units deviates from periodic ordering up to statistical stacking sequences.

For AEI and CHA structure type molecular sieves, the Periodic Building Unit is a double six ring layer. There are two types of layers "a" and "b", which are topologically identical except "b" is the mirror image of "a". When layers of the same type stack on top of one another, i.e., aaa or bbb, the framework type CHA is generated. When layers "a" and "b" alternate, i.e., abab, the framework type AEI is generated. Intergrowths of AEI and CHA structure molecular sieves comprise stackings of layers "a" and "b" containing regions of CHA structure type and regions of AEI structure type. Each change of CHA to AEI structure type is a stacking disorder or planar fault.

In the case of crystals with planar faults, the interpretation of X-ray diffraction patterns requires an ability to simulate the effects of stacking disorder. DIFFaX is a computer program based on a mathematical model for calculating intensities from crystals containing planar faults (see M. M. J. Tracey et al., Proceedings of the Royal Chemical Society, London, A [1991], Vol. 433, pp. 499-520). DIFFaX is the simulation program selected by and available from the International Zeolite Association to simulate the XRD powder patterns for intergrown phases of zeolites (see "Collection of Simulated XRD Powder Patterns for Zeolites" by M. M. J. Treacy and J. B. Higgins, 2001, Fourth Edition, published on behalf of the Structure Commission of the International Zeolite Association). It has also been used to theoretically study intergrown phases of AEI, CHA and KFI, as reported by K. P. Lillerud et al. in "Studies in Surface Science and Catalysis", 1994, Vol. 84, pp. 543-550.

Examples of aluminophosphate and metalloaluminophosphate molecular sieves comprising intergrown phases of AEI and CHA structure types include EMM-2, which is described in detail in International Patent Publication No. WO 02/70407, and RUW-19, which is described in detail in U.S. Pat. No. 6,334,994. The entire contents of these publications are incorporated herein by reference.

The synthesis method employed herein to produce the desired AEI structure type-containing molecular sieves can comprise:

a) forming a reaction mixture by combining a source of water, a source of aluminum (e.g., alumina, or a compound comprising a source of alumina), optionally a source of a metal other than aluminum (normally a source of silicon, e.g., silica, or a source of silica), a source of phosphorus (e.g., phosphoric acid, a diluted and/or aqueous phosphoric acid solution, phosphorus oxide, or the like), and at least one organic directing agent (template) for directing the formation of the desired molecular sieve;

b) heating the reaction mixture (a) at a controlled rate to a crystallization temperature of at least 150° C., for example between about 150° C. and about 200° C., such as between about 150° C. and about 175° C. or between about 155° C. and 170° C.;

c) maintaining the reaction mixture at the crystallization temperature for a period of time of at least 2 hours, for example from about 2 to about 150 hours, such as from about 5 hours to about 100 hours or from about 10 hours to about 50 hours; and (d) recovering a aluminophosphate or metalloaluminophosphate comprising an AEI structure type molecular sieve.

As described herein, the molecular sieve components (particularly the phosphorus, aluminum, and optionally other metal components) can have molar ratios relative to each other that are expressed in terms of their component oxides (e.g., $P_2O_5$, $Al_2O_3$, $SiO_2$, etc.), even though the actual source of those components may not actually be added in the oxide form or actually transform into an oxide form (for instance, the phosphorus-to-aluminum molar ratio is expressed herein as $P_2O_5$:$Al_2O_3$, even though the source of phosphorus may be added to the mixture as (aqueous) phosphoric acid, for example, and not as $P_2O_5$, and/or even though the source of aluminum may be added to the mixture as aluminum hydroxide ($Al(OH)_3$), for example, and not as $Al_2O_3$).

Generally, the reaction mixture formed in (a) has a molar ratio within the following ranges:

$P_2O_5$: $Al_2O_3$ from about 0.6 to about 1.2,
R:$Al_2O_3$ from about 0.5 to about 2, and
$H_2O$:$Al_2O_3$ less than 30.

The final molecular sieve is typically a metalloaluminophosphate (normally a SAPO or silicoaluminophosphate), the reaction mixture typically having a $M_{n/2}O$ : $Al_2O_3$ ratio from about 0.005 to about 0.6, where M is a metal, normally silicon, with a valence of n.

The rate of heating employed in step (b) is dependent on the $H_2O$:$Al_2O_3$ molar ratio of the reaction mixture (a). In a first embodiment, the $H_2O$:$Al_2O_3$ molar ratio of the reaction mixture is not constrained, although is generally less than 40, such as between about 10 to about 25, and the heating rate controlled so as to raise the temperature of the reaction mixture less than or equal to 6.0° C. per hour, such as at a first rate of between about 2° C. per hour and about 5° C. per hour, during at least part of the heating step and preferably for the entire heating to the crystallization temperature. In a second embodiment, the $H_2O$:$Al_2O_3$ molar ratio of the reaction mixture is between about 10 to about 25, and the heating rate controlled so as to raise the temperature of the reaction mixture less than or equal to 20° C. per hour, such as at a first rate of between about 2° C. per hour and about 15° C. per hour, for example at a rate of between about 2° C. per hour and about 5° C. per hour, during at least part of the heating step and preferably for the entire heating to the crystallization temperature.

As used in any of the embodiments herein, it should be understood that the phrase "at least part of the heating" should refer to a duration more than merely instantaneous and, indeed, to a relatively significant duration of time (e.g., at least one hour). In a preferred embodiment, the at least part of the heating can advantageously represent a duration of at least 5 hours, for example, at least 7 hours, at least 10 hours, at least 15 hours, or at least 20 hours. Without being bound by theory, because the duration during and/or immediately prior to crystallization is believed to be the most sensitive to heating rate, in a preferred embodiment, the at least part of the heating encompasses at least the duration of time during and/or immediately prior to crystallization. Additionally or alternately, instead of referring directly to the duration of time, the at least part of the heating can refer to a temperature range. Again, without being bound by theory, because the temperature during and/or immediately prior to crystallization is believed to be the most sensitive to heating rate, in a preferred embodiment, the at least part of the heating encompasses at least the last hour before attaining the crystallization temperature, for example at least the last 2 hours, at least the last 3 hours, at least the last 5 hours, at least the last 7 hours, at least the last 10 hours, at least the last 15 hours, or at least the last 20 hours. Alternately in this embodiment, the at least part of the heating encompasses at least one of the last 3 hours before attaining the crystallization temperature, for example at least 2 of the last 3 hours, at least 3 of the last 5 hours, at least 4 of the last 5 hours, at least 4 of the last 7 hours, at least 5 of the last 7 hours, at least 6 of the last 7 hours, at least 5 of the last 10 hours, at least 7 of the last 10 hours, at least 8 of the last 10 hours, at least 9 of the last 10 hours, at least 8 of the last 15 hours, at least 10 of the last 15 hours, at least 12 of the last 15 hours, at least 13 of the last 15 hours, at least 14 of the last 15 hours, at least 10 of the last 20 hours, at least 12 of the last 20 hours, at least 14 of the last 20 hours, at least 15 of the last 20 hours, at least 17 of the last 20 hours, at least 18 of the last 20 hours, or at least 19 of the last 20 hours.

In another embodiment, the reaction mixture can be maintained in step c) within the crystallization temperature range for a period of time of at least 2 hours, for example at least 3 hours, at least 5 hours, at least 10 hours, at least 15 hours, at least 20 hours, from about 2 to about 200 hours, from about 2 to about 150 hours, from about 5 hours to about 100 hours, or from about 10 hours to about 50 hours.

Preferably, the synthesis mixture is agitated (i.e., mixed, stirred, tumbled, shaken, swung, or any other mode of agitation) while the reaction mixture is heated up to the crystallization temperature. Agitation is preferably applied with an intensity that avoids precipitation of the synthesis mixture components. Hence the intensity of agitation may vary, depending on the physical and chemical nature of the components. Optionally, agitation may also be applied during all or part of the crystallization period.

The crystallization time in step c) will vary depending on the crystallization temperature, but the crystallization time should be sufficient to obtain substantially complete crystallization. Surprisingly, it has been found that, by reducing the rate of heating to the crystallization temperature, the yield of the desired AEI structure type-containing molecular sieve produced at any given crystallization temperature can be increased. Moreover, it has been found that this increase in yield can be maximized when the $H_2O$:$Al_2O_3$ molar ratio is also reduced, although excessive reduction in the ratio $H_2O$:$Al_2O_3$ molar ratio can be disadvantageous, particularly when it results in excessively viscous mixtures that are difficult to process. In fact, by suitable control of the crystallization conditions and of the composition of the reaction mixture, it is possible for the first time to produce an AEI/CHA intergrown molecular sieve at a yield of at least 18 wt %, such as at least 20 wt %, even in excess of 22 wt %, of the solids content of the reaction mixture.

The sources of the starting materials used to produce the reaction mixture (a) are not closely controlled, but examples of suitable aluminum sources can include, though are not limited to, hydrated aluminum oxides such as boehmite and pseudoboehmite, especially pseudoboehmite. Generally, the source of phosphorus is a phosphoric acid, especially orthophosphoric acid, but other sources, for example, organic phosphates, e.g., triethyl phosphate, and aluminophosphates may also be used. Where the reaction mixture (a) includes a source of silicon, suitable silicon sources can include, but are not limited to, colloidal silica, fumed silica, and organic silica sources such as tetraalkyl orthosilicates, especially tetraethyl orthosilicate.

The organic structure directing agent can conveniently include a tetraethyl ammonium compound, such as tetraethyl ammonium hydroxide (TEAOH), tetraethyl ammonium phosphate, tetraethyl ammonium fluoride, tetraethyl ammonium bromide, tetraethyl ammonium chloride or tetraethyl ammonium acetate. In one preferred embodiment, the directing agent includes tetraethyl ammonium hydroxide. In some cases, more than one organic structure directing agent may be employed, such as a combination of a tetraethyl ammonium compound and another nitrogen-containing compound such as dipropylamine.

Synthesis of the desired molecular sieve may be facilitated by the presence of at least 0.1 ppm, such as at least 10 ppm, for example at least 100 ppm or at least 500 ppm of seed crystals, based on total weight of the reaction mixture. The seed crystals can be homostructural with the desired AEI structure type-containing molecular sieve, for example the product of a previous synthesis, or can be a heterostructural crystalline material, such as an AEI, LEV, CHA, ERI, or combination structure-type molecular sieve.

Once crystallization is complete, the molecular sieve product can be recovered from the aqueous reaction medium, e.g., by any standard means, such as by centrifugation or filtration. If desired, the mother liquor remaining after removal of the crystalline product can be recycled to the mixture (a), so as to ensure effective utilization of the starting materials, and in particular the organic directing agent.

As a result of the crystallization process, the recovered crystalline product typically contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by other means, e.g., such as a conventional desorption process.

Once the intergrown crystalline material of the invention has been synthesized, it can be formulated into a catalyst composition by combination with other materials, such as binders and/or matrix materials, that provide additional hardness or catalytic activity to the finished catalyst.

Materials which can be blended with the intergrown crystalline material of the invention can be various inert or catalytically active materials. These materials can include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of intergrown crystalline material contained in the final catalyst product ranges from 10 to 90 weight percent of the total catalyst, for example 20 to 80 weight percent of the total catalyst.

The intergrown crystalline material described herein can be used to dry gases and liquids; for selective molecular separation based on size and polar properties; as an ion-exchanger; as a catalyst in organic conversion reactions, such as cracking, hydrocracking, disproportionation, alkylation, isomerization, oxidation, and synthesis of monoalkylamines and dialkylamines; as a chemical carrier; in gas chromatography; and in the petroleum industry to remove normal paraffins from distillates.

In particular, the intergrown crystalline material described herein is useful in the catalytic conversion of oxygenates, particularly alcohols such as methanol, to one or more olefins, particularly ethylene and propylene.

As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$ to $C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In such an oxygenate conversion process, a feedstock comprising an organic oxygenate, optionally with one or more diluents, can be contacted in the vapor phase in a reaction zone with a catalyst comprising the present molecular sieve at effective process conditions so as to produce (preferably at least 50 wt % or at least 60 wt %, based on the weight of the total product slate, of) the desired olefins. Alternatively, the process may be carried out in a liquid phase or in a mixed vapor/liquid phase. When the process is carried out in the liquid phase or a mixed vapor/liquid phase, different conversion rates and selectivities of feedstock-to-product may result, depending upon the catalyst and the reaction conditions.

When present, the diluent(s) is(are) generally non-reactive to the feedstock or molecular sieve catalyst composition and is(are) typically used to reduce the concentration of the oxygenate in the feedstock. Non-limiting examples of suitable diluents can include helium, argon, nitrogen, carbon monoxide, carbon dioxide, water, essentially non-reactive paraffins (especially alkanes such as methane, ethane, and propane), essentially non-reactive aromatic compounds, and mixtures thereof. Preferred diluents can include water and nitrogen, with water being particularly preferred. Diluent(s), when present, may comprise from about 1 mol % to about 99 mol % of the total feed mixture, though rarely comprising 50 mol% or more of the total feed mixture.

The temperature employed in the oxygenate conversion process may vary over a wide range, such as from about 200° C. to about 1000° C, for example from about 250° C. to about 800° C. or from about 250° C. to about 750° C., conveniently from about 300° C. to about 650° C. or from about 350° C. to about 600° C., or particularly from about 400° C. to about 600° C.

Light olefin products typically form, although not necessarily in optimum amounts, at a wide range of pressures, including, but not limited to, autogenous pressures and pressures in the range from about 0.1 kPa to about 10 MPa. Conveniently, the pressure can be in the range from about 7 kPa to about 5 MPa, such as from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene and/or propylene still may form.

A wide range of weight hourly space velocities (WHSV) for the feedstock can function in the oxygenate conversion process. WHSV is defined as the weight of feed (excluding diluent) per hour per weight of a total reaction volume of molecular sieve catalyst (excluding inerts and/or fillers). The WHSV generally should be in the range from about 0.01 $hr^{-1}$ to about 500 $hr^{-1}$, such as from about 0.5 $hr^{-1}$ to about 300 $hr^{-1}$, for example from about 0.1 $hr^{-1}$ to about 200 $hr^{-1}$.

A practical embodiment of a reactor system for the oxygenate conversion process is a circulating fluid bed reactor with continuous regeneration. Fixed beds are generally not preferred for the process, because oxygenate to olefin conversion is a highly exothermic process, which tends to require several stages with intercoolers or other cooling devices. The reaction also typically results in a high pressure drop, due to the production of low pressure, low density gas.

Additionally or alternately, the invention can include the following embodiments.

Embodiment 1

A method of synthesizing an aluminophosphate or metalloaluminophosphate molecular sieve comprising an AEI structure type material, the method comprising: (a) preparing a mixture comprising a source of water, a source of aluminum, optionally a source of a metal other than aluminum, a source of phosphorus, and at least one organic directing agent for directing the formation of said molecular sieve; (b) heating said mixture to a crystallization temperature of between 150° C. and 200° C., wherein at least part of said heating is conducted so as to raise the temperature of said mixture at a rate of less than or equal to 6.0° C. per hour, preferably a non-zero rate; (c) maintaining said mixture at said crystallization temperature for a period of time from 2 to 150 hours; and (d) recovering said molecular sieve.

Embodiment 2

The method of embodiment 1, wherein said mixture in (a) has a $H_2O:Al_2O_3$ molar ratio less than 40.

Embodiment 3

A method of synthesizing an aluminophosphate or metalloaluminophosphate molecular sieve comprising an AEI structure type material, the method comprising: (a) preparing a mixture comprising a source of water, a source of aluminum, optionally a source of a metal other than aluminum, a source of phosphorus, and at least one organic directing agent (R) for directing the formation of said molecular sieve, said mixture having the following molar composition:
  $P_2O_5: Al_2O_3$ from about 0.6 to about 1.2,
  R: $Al_2O_3$ from about 0.5 to about 2, and
  $H_2O:Al_2O_3$ less than 30;
(b) heating said mixture to a crystallization temperature of between about 150° C. and about 200° C., wherein at least part of said heating is conducted so as to raise the temperature of said mixture at a rate of less than or equal to 20° C. per hour, preferably a non-zero rate; (c) maintaining said mixture at said crystallization temperature for a period of time from about 2 to about 150 hours; and (d) recovering said molecular sieve.

Embodiment 4

The method of embodiment 3, wherein at least part of said heating is conducted so as to raise the temperature of said mixture at a rate of between 2° C. per hour and 15° C. per hour.

Embodiment 5

The method of any preceding embodiment, wherein at least part of said heating is conducted so as to raise the temperature of said mixture at a rate between 2° C. per hour and 5° C. per hour.

Embodiment 6

The method of any preceding embodiment, wherein said mixture in (a) has a $H_2O:Al_2O_3$ molar ratio between about 10 to about 25.

Embodiment 7

The method of any preceding embodiment, wherein said mixture includes a source of a metal other than aluminum, and preferably silicon.

Embodiment 8

The method of embodiment 7, wherein said mixture (a) has a $M_{n/2}O: Al_2O_3$ ratio of from about 0.005 to about 0.6 where M is said metal other than aluminum and has a valence n.

Embodiment 9

The method of any preceding embodiment, wherein said mixture is agitated during (b) and (c).

Embodiment 10

A method of synthesizing an aluminophosphate or metalloaluminophosphate molecular sieve comprising at least one intergrown phase of an AEI structure type material and a CHA structure type material, the method comprising crystallizing a reaction mixture comprising a source of water, a source of aluminum, optionally a source of a metal other than aluminum, a source of phosphorus, and at least one organic directing agent (R) for directing the formation of said molecular sieve, wherein the conditions of said crystallizing are controlled so that the yield of said molecular sieve is at least 18 wt %, preferably at least 20 wt %, of the solids content of the reaction mixture.

Embodiment 11

The method of any preceding embodiment, wherein said at least one organic directing agent comprises a tetraethylammonium compound.

Embodiment 12

The method of any preceding embodiment, wherein the crystallization temperature is between about 150° C. and about 175° C.

Embodiment 13

The method of any preceding embodiment, wherein the crystallization time is from about 5 hours to about 100 hours.

Embodiment 14

An aluminophosphate or metalloaluminophosphate molecular sieve comprising an AEI structure type material produced by the method of any preceding embodiment.

Embodiment 15

A process for making an olefin product from an oxygenate feedstock comprising contacting said oxygenate feedstock with a catalyst comprising the aluminophosphate or metalloaluminophosphate molecular sieve of embodiment 14.

The invention will now be more particularly described with reference to the following non-limiting Examples.

EXAMPLES

Examples 1-2

Synthesis of SAPO-18

A mixture of phosphoric acid (85% in water, Acros), demineralized water, and tetraethylammonium hydroxide solution (35% in water, Sachem) was prepared. The resultant mixture was transferred to a reactor vial kept at about 30° C. under stirred conditions, and then Ludox AS 40 (40% silica in water, Grace), followed by alumina (Condea Pural SB, 75.6 wt % $Al_2O_3$), was added to the mixture with continuous stirring. A slurry was produced and was then aged for 2 hours at about 30° C., with the stirring being continued. The composition of the slurry in terms of molar ratios was as follows:

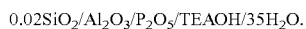

The aged slurry mixture was divided into 2 samples, which were heated in stirred reactors under autogenous pressure at ramp rates of about 20° C./hour and 5° C./hour, respectively, to a crystallization temperature of about 165° C. The reactors were maintained at the crystallization temperature for about 72 hours, after which the reactors were cooled to room temperature and the crystals separated from the mother liquor by centrifuging. The crystals were subsequently washed several times with de-mineralized water. The washed crystals were dried overnight at about 120° C., and the resultant product was weighted. The results are shown in Table 1, in which the yield is expressed as wt % of dried product, based on the total weight of the initial reaction mixture.

Example 3

Synthesis of SAPO-18

The process of Examples 1-2 was repeated, except the $H_2O$ : $Al_2O_3$ molar ratio of the reaction mixture was reduced to about 25, and the rate of heating to the crystallization temperature of about 165° C. was maintained at about 5° C./hour. These results are also shown in Table 1 below.

TABLE 1

| Ex. | Ramp (° C./hr) | Temp (° C.) | $H_2O$:$Al_2O_3$ | Product | Yield (%) |
|---|---|---|---|---|---|
| 1 | 20 | 165 | 35 | AEI | 15.0 |
| 2 | 5 | 165 | 35 | AEI | 18.8 |
| 3 | 5 | 165 | 25 | AEI | 19.8 |

It can be seen from the results in Table 1 that the yield of AEI product was significantly increased by reducing the heat-up rate from about 20° C./hour to about 5° C./hour. The yield was further increased by reducing the water content of the reaction mixture, while keeping the heat-up rate the same at about 5° C./hour.

Examples 4-9

Synthesis of AEI/CHA Intergrowth

The procedure of Examples 1-2 was repeated with the reaction mixture having the following molar composition:

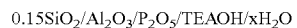

where x was 35 or 25.

After aging, the resultant slurries were heated at ramp rates of about 20° C./hour or about 5° C./hour, respectively, to a crystallization temperature of about 165° C. or about 170° C., respectively, and crystallized for about 72 hours (crystallization temperature of 165° C.) or about 48 hours (crystallization temperature of 170° C.). The results are shown in Table 2 below.

TABLE 2

| Ex. | Ramp (° C./hr) | Temp (° C.) | $H_2O$:$Al_2O_3$ | Product | Yield (%) |
|---|---|---|---|---|---|
| 4 | 20 | 165 | 35 | AEI/CHA | 19.3 |
| 5 | 20 | 165 | 25 | AEI/CHA | 19.9 |
| 6 | 20 | 170 | 25 | AEI/CHA + AFI | 23.9 |
| 7 | 5 | 165 | 35 | AEI/CHA | 23.3 |
| 8 | 5 | 165 | 25 | AEI/CHA | 26.2 |
| 9 | 2 | 165 | 35 | AEI/CHA | 24.9 |

The results in Table 2 show that, by reducing the water content of the synthesis mixture, the yield was increased (compare Example 4 to Example 5 and Example 7 to Example 8). Another incremental yield increase was obtained by increasing the crystallization temperature to about 170° C. (see Example 6), but this was accompanied by the production of an AFI structure type impurity. The crystallization yield of the pure AEI/CHA intergrowth was increased at the crystallization temperature of about 165° C. by reducing the heat-up rate (compare Example 5 to Example 8 and Example 4 to Example 7 to Example 9).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

What is claimed is:

1. A process for making an olefin product from an oxygenate feedstock comprising:
   (1) synthesizing an aluminophosphate or metalloaluminophosphate molecular sieve comprising an AEI structure type material by
      (a) preparing a mixture comprising a source of water, a source of aluminum, a source of phosphorus, and at least one directing agent, wherein the ratio of $H_2O$:$Al_2O_3$ is less than 30,
      (b) heating said mixture to a crystallization temperature within a range of from about 150° C. to about 200° C., wherein at least part of said heating is conducted so as to raise the temperature of said mixture at a rate of 6.0° C. per hour or less, said temperature raising extending for at least one hour,
      (c) maintaining said mixture within the crystallization temperature range for a time from about 5 hours to about 100 hours, wherein said mixture is agitated during steps (b) and (c), and
      (d) recovering said molecular sieve at a yield of at least 18 wt %; and
   (2) contacting said oxygenate feedstock with a catalyst comprising said molecular sieve to produce an olefin product.

2. The method of claim 1, wherein at least part of said heating is conducted so as to raise the temperature of said mixture at a rate between about 2° C. per hour and about 5° C. per hour.

3. The method of claim 1, wherein said mixture in (a) has a $H_2O$:$Al_2O_3$ molar ratio between about 10 to about 25.

4. The method of claim 1, wherein said mixture includes a source of an oxide of a metal other than aluminum.

5. The method of claim 1, wherein said metal other than aluminum is silicon.

6. The method of claim 1, wherein said crystallization temperature is between about 150° C. and about 175°.

7. A process for making an olefin product from an oxygenate feedstock comprising:
   (1) synthesizing an aluminophosphate or metalloaluminophosphate molecular sieve comprising an ALT structure type material by
      (a) preparing a mixture comprising a source of water, a source of aluminum, optionally a source of a metal other than aluminum, a source of phosphorus, and at least one organic directing agent (R) for directing the formation of said molecular sieve, said mixture having the following molar composition:
         $P_2O_5$:$Al_2O_3$ from about 0.6 to about 1.2,
         R:$Al_2O_3$ from about 0.5 to about 2, and
         $H_2O$:$Al_2O_3$ between about 10 to about 25,
      (b) heating said mixture to a crystallization temperature of between about 150° C. and about 20° C., wherein at least part of said heating is conducted so as to raise the temperature of said mixture at a rate of less than or equal to 6° C. per hour,
      (c) maintaining said mixture at said crystallization temperature for a crystallization time from about 5 hours to about 100 hours, wherein said mixture is agitated during steps (b) and (c), and
      (d) recovering said molecular sieve at a yield of at least 18 wt %; and
   (2) contacting said oxygenate feedstock with a catalyst comprising said molecular sieve to produce an olefin product.

* * * * *